(12) United States Patent
Herman

(10) Patent No.: US 7,909,757 B2
(45) Date of Patent: Mar. 22, 2011

(54) LARYNGOSCOPE BLADE

(76) Inventor: Dwight Herman, Denison, TX (US)

( * ) Notice: Subject to any disclaimer, the term of this patent is extended or adjusted under 35 U.S.C. 154(b) by 934 days.

(21) Appl. No.: 11/397,835

(22) Filed: Apr. 3, 2006

(65) Prior Publication Data

US 2007/0232862 A1    Oct. 4, 2007

(51) Int. Cl.
*A61B 1/267* (2006.01)
(52) U.S. Cl. .......... 600/190; 600/185; 600/199
(58) Field of Classification Search .......... 600/190–196; D24/137, 135
See application file for complete search history.

(56) References Cited

U.S. PATENT DOCUMENTS

| | | | | |
|---|---|---|---|---|
| 4,527,553 A | * | 7/1985 | Upsher | 600/188 |
| 4,827,910 A | * | 5/1989 | Mathews, III | 600/194 |
| 4,947,896 A | * | 8/1990 | Bartlett | 600/187 |
| 4,982,729 A | * | 1/1991 | Wu | 600/187 |
| 5,065,738 A | * | 11/1991 | Van Dam | 600/185 |
| 5,174,283 A | * | 12/1992 | Parker | 128/200.26 |
| 6,311,688 B1 | * | 11/2001 | Augustine et al. | 128/200.26 |
| RE37,861 E | | 9/2002 | Schneider | |
| D491,267 S | | 6/2004 | Ashraf | |

* cited by examiner

*Primary Examiner* — Eduardo C Robert
*Assistant Examiner* — Julianna N Harvey
(74) *Attorney, Agent, or Firm* — Lynn E. Barber

(57) ABSTRACT

A blade for a laryngoscope having a handle, the blade having an elongated body having a central axis, and having a distal tip symmetric about the central axis; a downwardly convex arcuate central portion including a first flange and a second flange is disclosed herein. Each flange has a distal flange tip and a proximal base, the first flange tip being a mirror image of the second flange about the central axis. The outer edge of the base of the first flange is convex and the outer edge of the base of the second flange is concave with respect to the central axis. A light attachment area is provided along the central axis. The distal tip may have any one of a variety of shapes, including having outer rounded lobes, being generally rectangular, or having a spoon shape.

7 Claims, 6 Drawing Sheets

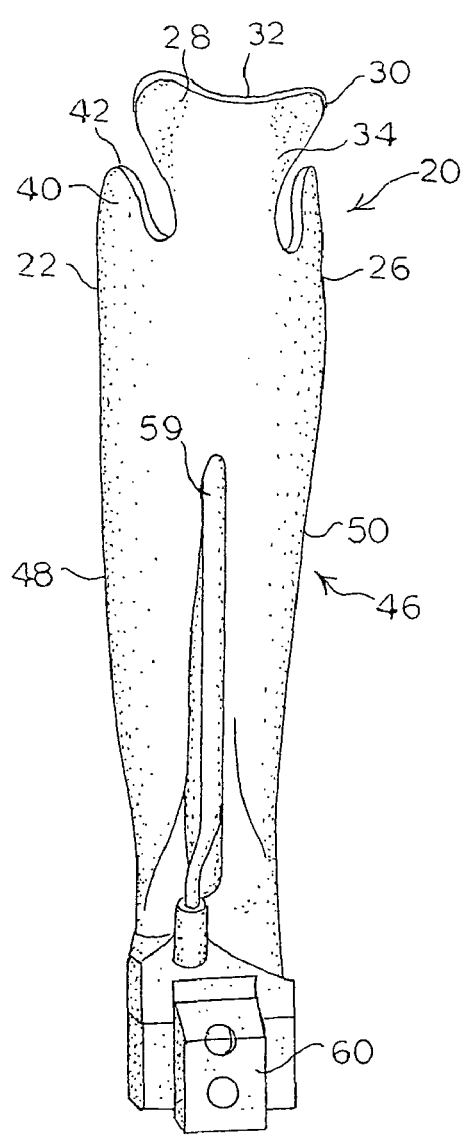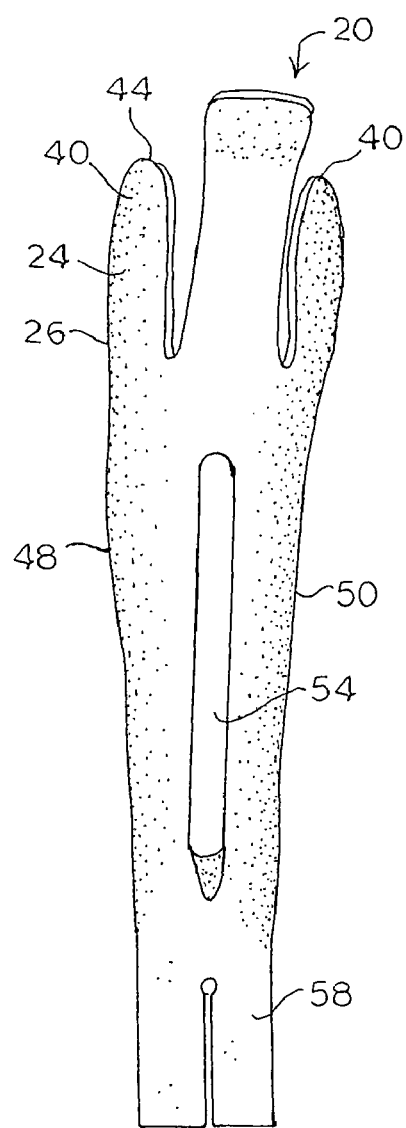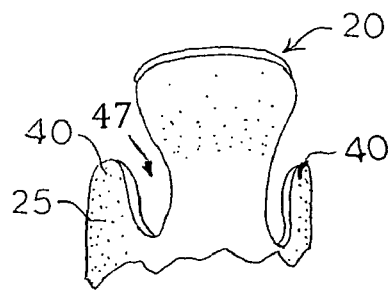

LARYNGOSCOPE BLADE

BACKGROUND OF THE INVENTION

1. Field of the Invention

This invention relates to laryngoscopes, and in particular, relates to laryngoscope blades.

2. Description of the Related Art

Laryngoscopes are used to establish an artificial airway in a respiratory compromised person by exposing the glottic opening through displacing the tongue and orpharyngeal tissue, illuminating of the laryngeal opening, and providing tongue and epiglottis stability. Thus, a laryngoscope allows examination of the larynx and aids in endotracheal intubation, such as during surgery or to assist patients to breathe in emergency situations. During intubation, a flexible tube is inserted over the tongue, through the larynx past the vocal cords and epiglottis. It is important in use of a laryngoscope that the blade be structured to keep the tongue and epiglottis from occluding the view of the vocal cords without harming the patient's delicate soft tissue.

Two commonly used laryngoscope blades are the Miller blade and the Macintosh blade. The Miller blade is a relatively narrow straight blade with a slightly elevated tip. This blade sweeps the tongue to the side and lifts the epiglottis directly to allow visualization of the vocal cords so that the tube may be inserted correctly. The Macintosh blade is a wider curved blade, and is used by placing the tip between the epiglottis and the base of the tongue (valecula) and placing pressure to raise the epiglottis enough so that the vocal cords may be viewed.

The structure of these and other prior blades often makes it difficult to see down the patient's throat, due to portions of the structure, such as the light source or blade tip, blocking the area that the practitioner is trying to observe or blocking view of the passageway. Some prior structures often do not sufficiently displace the tongue, epiglottis, and oropharynx for optimal use.

It is therefore an object of the invention to provide a new laryngoscope blade that features a new curved form with bilateral flanges so that it better displaces oropharyngeal soft tissue and gives a larger, more direct view of the glottic opening, especially in Mallampati class III and IV airways (classification of airway during pre-operative examination of patient) where there is an inability to visualize certain pharyngeal structures. This can make for a more challenging orotracheal intubation. The laryngoscope blade of the invention also provides better stability of the tongue and epiglottis during use.

Other objects and advantages will be more fully apparent from the following disclosure and appended claims.

SUMMARY OF THE INVENTION

The invention herein is a blade for a laryngoscope having a handle, the blade having an elongated body having a central axis, and having a distal tip symmetric about the central axis; a downwardly convex arcuate central portion including a first flange and a second flange. Each flange has a distal flange tip and a proximal base, the first flange tip being a mirror image of the second flange about the central axis. The outer edge of the base of the first flange is convex and the outer edge of the base of the second flange is concave with respect to the central axis. A light attachment area is provided along the central axis.

Other objects and features of the inventions will be more fully apparent from the following disclosure and appended claims.

BRIEF DESCRIPTION OF THE DRAWINGS

FIG. 1 is a top perspective view of a first embodiment of the laryngoscope blade of the invention.

FIG. 2 is a top plan view of a second embodiment of the laryngoscope blade of the invention.

FIG. 3 is a top plan view of the distal end of a third embodiment of the laryngoscope blade of the invention.

DETAILED DESCRIPTION OF THE INVENTION AND PREFERRED EMBODIMENTS THEREOF

The present invention is a laryngoscope blade having a flanged structure that compresses the tongue and oropharynx anteriorly as well as displacing the bulk of the tongue distally left and right with the tongue going equally both ways at the same time. A first embodiment 22 of the invention with a straight tip and a third embodiment 25 with a spoon tip is particularly useful for direct manipulation of the epiglottis, while a second embodiment 24 with a curved tip is particularly useful for manipulating the epiglottis via the valecula.

Figure 15:
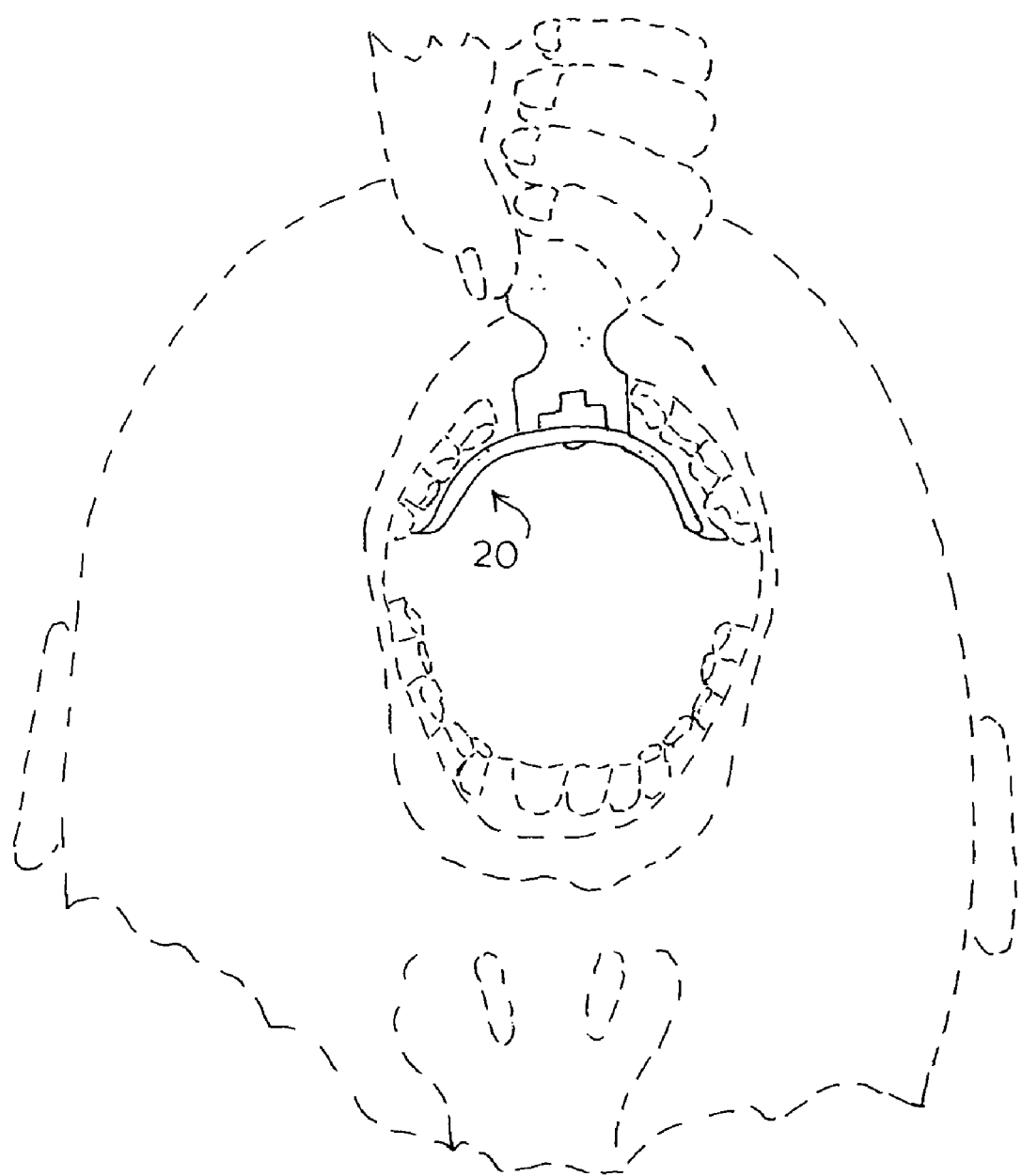
FIG. 15 is a perspective view of use of the blade of the invention.

As used herein, the term "downward" or "below" refer to the side of the invention that is inferior (roof of mouth) when the blade is inserted into the throat of a supine person, as shown in FIG. 15. The term "distal" refers to portions of the blade away from the handle, and the term "proximal" refers to portions of the blade closer to the handle.

The laryngoscope blade 20 of the invention may be made of different materials, and is preferably made out of stainless steel, plastic (disposable), or other metals that may be formed into the structure disclosed herein and may be safely used in the mouth. It may be constructed in different sizes and dimensions to accommodate adult and pediatric airways. In addition, the blade 20 may be configured with different light sources (conventional, fiberoptic, and the like) attached to the blade as in the same way as is known in the art, with or without suction apparatus, with or without a tongue gripping apparatus and with or without an epiglottal stabilizing design.

The laryngoscope blade 20 of the invention has three different preferred embodiments of the blade tip: relatively straight tip of the first embodiment (FIGS. 1, 4, 6 and 7), curved tip (as viewed from the side) of the second embodiment (FIGS. 2, 5, 11 and 12), and spoon tip of the third embodiment (FIG. 3)(which would look like the first embodiment from the side). In each embodiment, as shown in the Figures, there is a gap 47 between each flange 40 and the tip.

Figure 4:
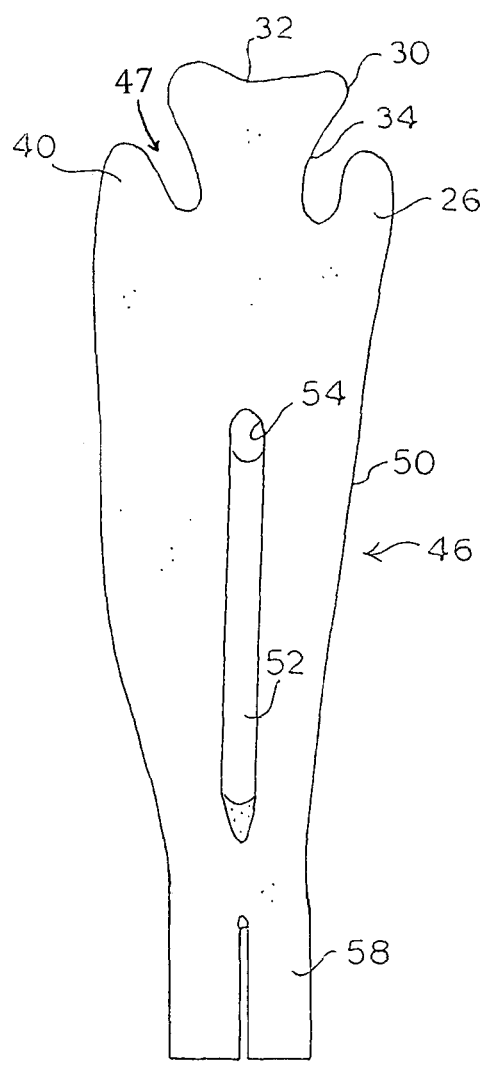
FIG. 4 is a top plan view of the template used to make the first embodiment of the laryngoscope blade of the invention.
Figure 5:
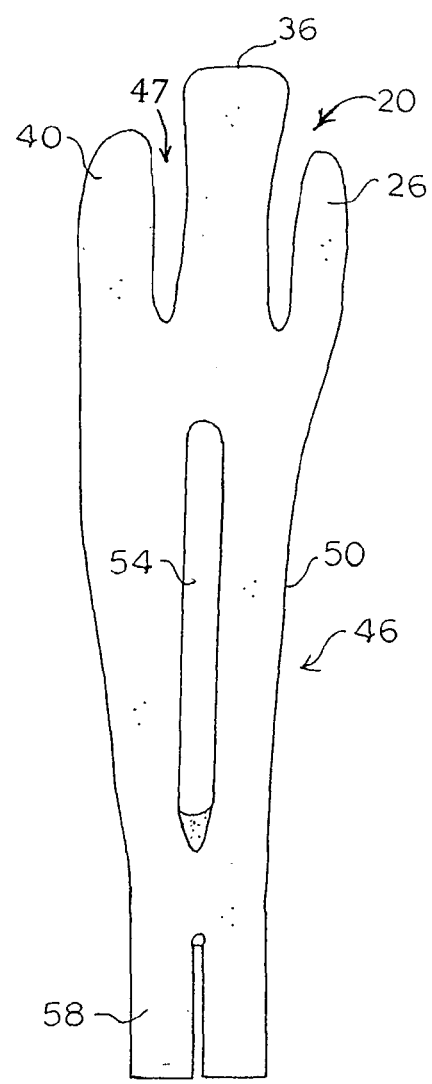
FIG. 5 is a top plan view of the template used to make the second embodiment of the laryngoscope blade of the invention.

When made of stainless steel, the laryngoscope blade 20 is cut out of a flat piece (preferably less than about 2 mm thick) of stainless steel in the shape shown in FIG. 4 for the first embodiment 22, and in FIG. 5 for the second embodiment 24. The blade is preferably about 153 mm long for an average to large woman and a small to large man, but it could be possibly 3 cm shorter or longer without affecting performance, since the width is more critical than the length of the blade. The body of the blade in this embodiment at its widest point 26, which is the area having the flanges 40, is preferably about 50 mm wide, and at its handle end is about 21 mm, to allow attachment to a standard laryngoscope blade handle.

Figure 6:
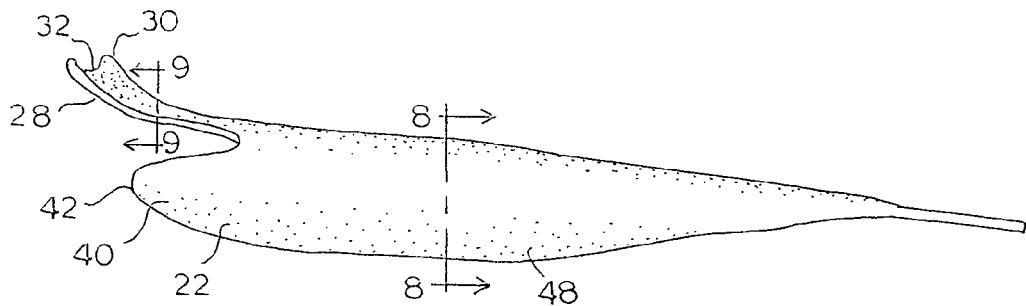
FIG. 6 is a left side perspective view of the first embodiment of the laryngoscope blade of the invention.
Figure 7:
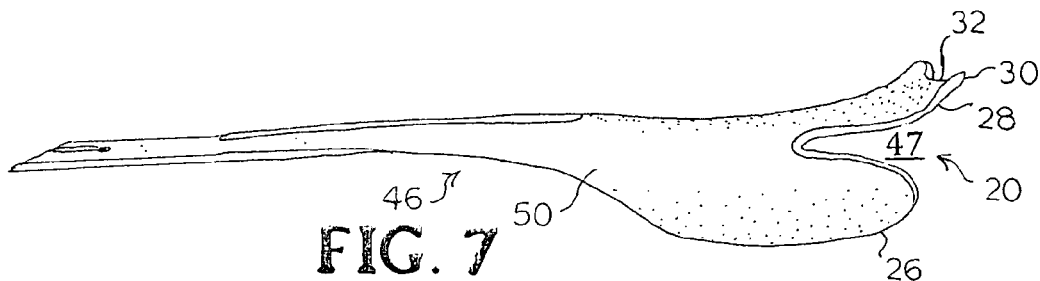
FIG. 7 is a right side perspective view of the first embodiment of the laryngoscope blade of the invention which is cut away as compared to the left side (FIG. 6).

In the first embodiment 22 of the invention herein, the tip 28 is slightly curved upward at the tip when viewed from the side (FIGS. 6-7). When viewed from above or below, the end of the tip 28 has two outer rounded lobes 30 and has a central inward concavity 32 (FIGS. 1 and 4). In any large adolescent to adult, the blade tip will accommodate the largest epiglottis (as a large male), and in doing so will also accommodate a smaller epiglottis (as a small adolescent or female). The width at the widest point of the blade should be no smaller than 36-42 mm. The length of the tip is preferably 28-32 mm, and at its narrowest point 34 this tip is preferably about 15.5 mm. This tip is particularly useful for manipulating the epiglottis. In use, viewing the epiglottis as the blade is inserted into the oropharynx, the tip scoops gently under the epiglottis and is lifted anteriorly, exposing the glottic opening so the endotracheal tube can pass via the opening.

Figure 19:
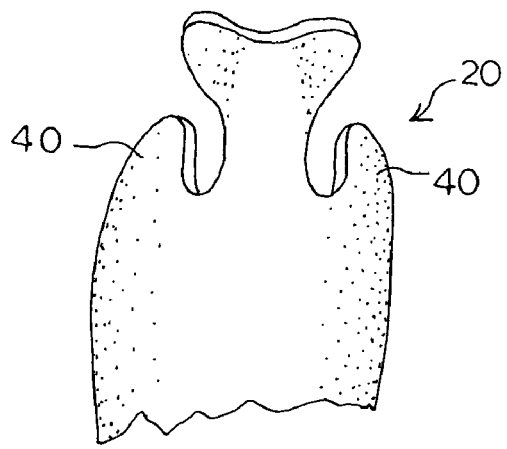
FIG. 19 is a top plan view of the distal end of a blade of the first embodiment having slightly tapered flanges.

In a variation of the first embodiment 22 shown in FIG. 19, the outer edge of flange 40 has a slight taper as can be seen by comparison of FIG. 19 with FIG. 1, which better ensures avoidance of trauma to the oropharyngeal walls when the blade is inserted.

Figure 11:
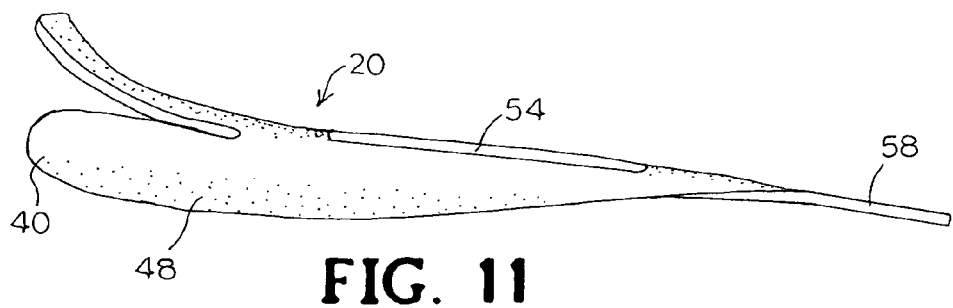
FIG. 11 is a left side perspective view of the second embodiment of the laryngoscope blade of the invention.
Figure 12:
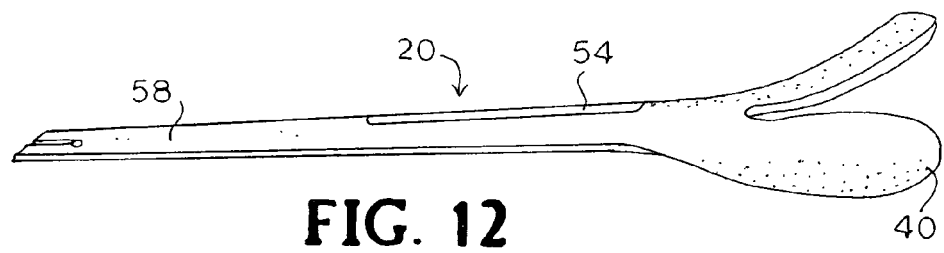
FIG. 12 is a right side perspective view of the second embodiment of the laryngoscope blade of the invention which is cut away as compared to the left side (FIG. 11).

In the second embodiment 24 of the invention herein, the tip 36 is curved when viewed from the side (FIGS. 11-12). When viewed from above or below (FIG. 2 for view from above), the end of the tip 36 in this embodiment is straight as shown, and the tip itself is generally in the form of an elongated rectangle. Preferably the tip of this blade is about 17 mm wide and 40 mm long. This tip is particularly useful for manipulating the valecula. In use, the epiglottis is visualized as the blade is inserted into the oropharynx. The tip is placed in the valecula (tissue area directly in front of the epiglottis) and is lifted anteriorly, causing the epiglottis to flip up (forward and anterior), exposing the glottic opening behind the epiglottis.

Figure 18:
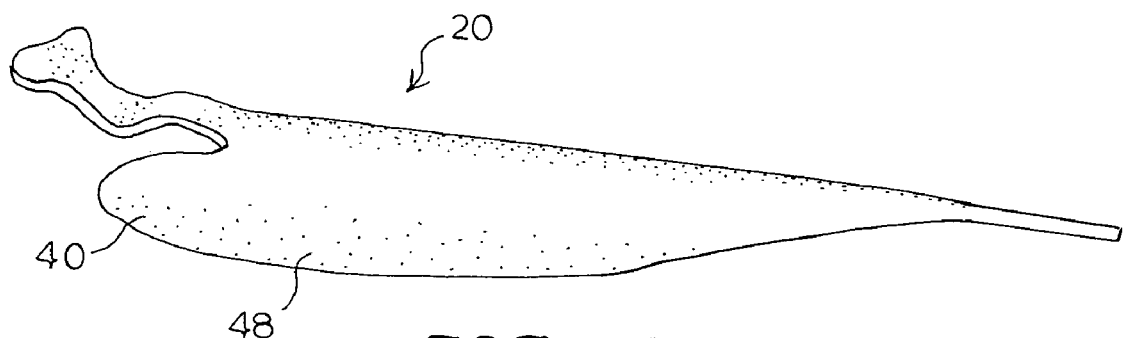
FIG. 18 is a left side perspective view of a tip of the first embodiment having an escalated shape.

In an alternative version of the tip of the invention, the tip may have an escalated shape as is shown in FIG. 18. This shape would enable the user to get a better anterior view due to the ultimate height of the tip being somewhat less above the body of the blade.

Figure 16:
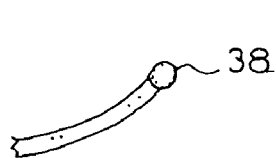
FIG. 16 is a side view of the protective nub on the tip of the second embodiment of the invention enlarged.
Figure 17:
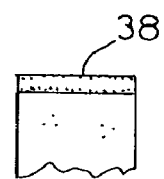
FIG. 17 is a top view of the protective nub on the tip of the second embodiment of the invention.

A protective nub 38 is most preferably placed at the tip 36 of the blade of the second embodiment 24 and is preferably made of the same material as the blade. Thus, for a steel blade, a second of steel wire having the same diameter as the thickness of the blade and a length as long as the width of the blade tip is welded to the end of the blade tip as shown in FIGS. 16-17 to form the nub 38.

In both primary embodiments of the invention herein, the blade has two flanges 40 to displace pharyngeal soft tissue. For the first (straight) embodiment 22 (FIG. 1) for use in a person having a large throat, the distal end 42 of each of these flanges 40 is the same size, which is preferably about 15 mm long and 11 mm wide. The distal ends 42 of the flanges 40 in this embodiment are preferably separated from the base of the tip by a gap 47 of about 6 mm. For the curved tip second embodiment 24, the distal end 44 of each of the flanges 40 is preferably about 30 mm long and about 8-9 mm wide (FIG. 2).

As can be seen in FIGS. 1-2, the blade is not symmetric about its central axis (shown in a dotted line), but rather has an open area 46 on the right side as viewed from above to allow easier viewing past the blade 20 when the blade is being used. This open area 46 can be more easily seen by comparing FIG. 6 with FIG. 7. This open area 46 allows the endotracheal tube to be placed with minimal visual obstruction. Thus, the base 48 of the left flange of each embodiment, as viewed in FIGS. 1 and 2, is convex outward as shown, while the base 50 of the right flange is concave inward. This configuration is preferred for a right-handed person, who typically uses the laryngoscope blade with the left hand, and inserts the endotracheal tube with the right hand; however, the mirror-image of the invention could be made without departing from the spirit and scope of the invention herein. Alternatively, both sides could be cut out, but this configuration would not be as useful in displacing soft tissue during use of the laryngoscope blade.

Figure 8:
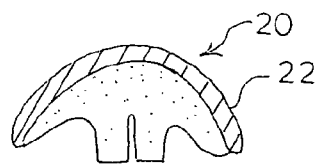
FIG. 8 is a cross-sectional view of FIG. 6 at 8-8.
Figure 9:
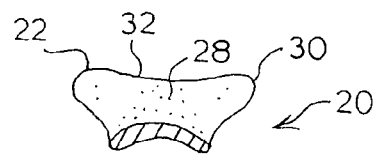
FIG. 9 is a cross-sectional view of FIG. 6 at 9-9.

A press rig or other device as is known in the art is used to attain a uniform curve to the blade. As shown in FIG. 8, the central area of the laryngoscope blade of the invention has a cross-section in the form of an arc, which due to the difference in flange base size, has differently sized arms. A cross-section taken closer to the tip of the flanges (FIG. 9) is shorter with same-length arms and less curvature than the central cross-section shows.

Figure 10:
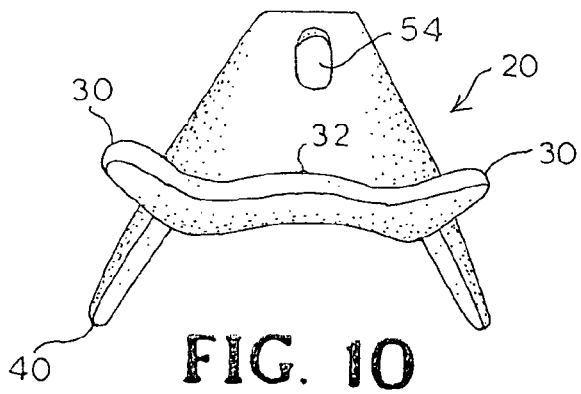
FIG. 10 is a distal end perspective view of the first embodiment.
Figure 13:
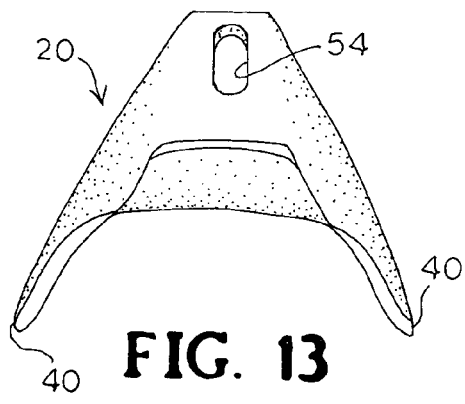
FIG. 13 is a distal end perspective view of the second embodiment.
Figure 14:
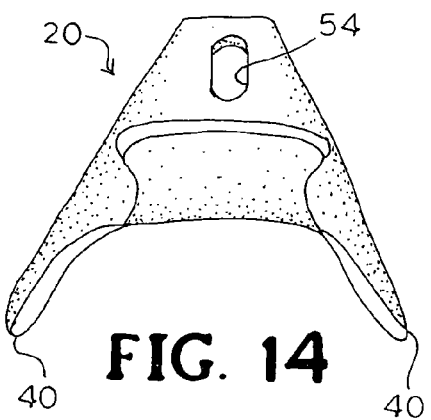
FIG. 14 is a distal end perspective view of the third embodiment.

An end view of the distal tip of the three embodiments is shown in FIGS. 10, 13 and 14, respectively. In the first embodiment (FIG. 10), the outer rounded points of the blade tip are elevated as shown. The distal ends 42 of the flanges 40 could be thickened and rounded using a soldering or welding technique to increase the surface area, and to decrease trauma to the soft oropharyngeal tissue.

The light source may be attached to the top of the blade in a variety of ways. In any case, the preferred arrangement is to have the light source run along the top of the blade in a trough before poking through the blade to the bottom of the blade about one-third of the way along the blade from the tip, to illuminate the oropharynx. In one preferred embodiment shown in FIG. 4, a trough (groove) 52 is pressed down the middle of the blade, extending about 70 mm and having a width of about 25 mm. A central hole 54 having a diameter of about 2.5 mm is located at the end of the groove for placement of the light source. Alternatively, a slot 56, 50 mm×2.5 mm, may be formed down the central axis of the blade as shown. In either case, the handle end 58 of the blade extends about 30-35 mm from the proximal end of the slot or trough.

The light source 59 (shown in FIG. 1), preferably a standard fiberoptic light source as is known in the art, is attached to the blade 20 by welding or soldering as is known in the art.

A standard handle connection fixture 60 is preferably attached to the handle end 58 of the blade 20 of the invention so that the laryngoscope blade of the invention may be used with standard handles known in the art, and the handle end 58 as shown in the figures is configured to attach thereto.

Optionally, a suction source, e.g., a metal tube, may be placed along the larger flange directing a disposable suction catheter toward the posterior oropharynx (not shown).

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A blade for a laryngoscope having a handle, the blade comprising an elongated body having a central axis, and having:
   a) a distal tip being symmetric about the central axis;
   b) a central portion having a downwardly convex arcuate cross-section, comprising:
      i) a first flange and a second flange, each flange having a distal flange tip and a proximal base with the distal flange tip of each flange being separated from the distal tip of the laryngoscope blade by a gap, the first flange tip being a mirror image about the central axis of the second flange tip; the outer edge of the base of the first flange being convex with respect to the central axis, and the outer edge of the base of the second flange being concave with respect to the central axis such that the base of the first flange is not a mirror image about the central axis of the base of the second flange; and
      ii) a light attachment area comprising an opening on the central axis and a trough on the top of the blade, wherein a source of light extends in the trough and through the opening to the bottom of the blade; and
   c) a proximal handle attachment portion.

2. The laryngoscope blade according to claim 1, wherein the distal tip of the laryngoscope blade has two outer rounded lobes and has a central inward concavity.

3. The laryngoscope blade according to claim 1, wherein the distal tip is an elongated rectangle.

4. The laryngoscope blade according to claim 3, further comprising a protective nub on the distal tip.

5. The laryngoscope blade according to claim 1, wherein the distal tip is spoon shaped.

6. The laryngoscope blade according to claim 1, wherein the opening is elongated.

7. The laryngoscope blade according to claim 1, wherein the outer edge of each flange tip is tapered inward toward the central axis.

* * * * *